(12) United States Patent  
Walborn (10) Patent No.: US 7,892,213 B2
(45) Date of Patent: Feb. 22, 2011

(54) FLUID FLOW CONTROL SYSTEM HAVING CAPILLARY FLUID FLOW RESTRICTOR

(75) Inventor: Jonathan Walborn, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 736 days.

(21) Appl. No.: 11/738,276

(22) Filed: Apr. 20, 2007

(65) Prior Publication Data

US 2008/0257410 A1  Oct. 23, 2008

(51) Int. Cl.
*A61M 5/00* (2006.01)

(52) U.S. Cl. ..................................... 604/246

(58) Field of Classification Search ... 604/890.1–892.1, 604/246
See application file for complete search history.

(56) References Cited

U.S. PATENT DOCUMENTS

| | | | |
|---|---|---|---|
| 4,209,014 A | 6/1980 | Sefton | |
| 4,505,701 A | 3/1985 | Navato | |
| 4,626,243 A * | 12/1986 | Singh et al. | 604/141 |
| 4,741,733 A | 5/1988 | Winchell et al. | |
| 4,904,239 A | 2/1990 | Winchell et al. | |
| 4,909,790 A | 3/1990 | Tsujikawa et al. | |
| 4,931,050 A | 6/1990 | Idriss | |
| 4,997,420 A | 3/1991 | LeFevre | |
| 5,011,477 A | 4/1991 | Wincell | |
| 5,053,031 A | 10/1991 | Borsanyi | |
| 5,178,610 A | 1/1993 | Tsujikawa | |
| 5,211,632 A | 5/1993 | Tsukada | |
| 5,219,334 A | 6/1993 | Tsukada | |
| 5,290,238 A | 3/1994 | Crass | |
| 5,336,194 A | 8/1994 | Polaschegg | |
| 5,447,672 A | 9/1995 | O'Neil | |
| 5,663,487 A | 9/1997 | Widt | |
| 5,716,343 A | 2/1998 | Kriesel | |
| 5,785,681 A | 7/1998 | Indravudh | |
| 5,820,565 A * | 10/1998 | McArthur | 600/486 |
| 5,885,250 A | 3/1999 | Kriesel | |
| 5,897,530 A | 4/1999 | Jackson | |
| 5,906,597 A | 5/1999 | McPhee | |
| 6,174,300 B1 | 1/2001 | Kriesel | |

(Continued)

FOREIGN PATENT DOCUMENTS

EP 295504 A * 12/1988

(Continued)

*Primary Examiner*—Nicholas D Lucchesi
*Assistant Examiner*—Diva Ranade
(74) *Attorney, Agent, or Firm*—McDermott Will & Emery LLP (57) ABSTRACT

A fluid flow rate control system and method comprises a capillary tube having a proximal end that projects into a chamber with a cross-sectional area that is larger than or equal to the fluid supply tube's cross-sectional area. The inner cross-sectional area of the capillary tube is configured less than the inner cross-sectional area of the chamber. The chamber has a volume large enough to slow the fluid conducted to it by the upstream fluid line to permit contaminants to fall out of solution. In another aspect, a sleeve is used to mount the capillary tube into the chamber. The sleeve provides a mounting surface for tube segments from the pump and downstream of the capillary restrictor.

6 Claims, 4 Drawing Sheets

U.S. PATENT DOCUMENTS

| | | | |
|---|---|---|---|
| 6,569,128 B1 * | 5/2003 | Christensen et al. | ........ 604/246 |
| 2002/0028308 A1 | 3/2002 | Harada | |
| 2004/0153029 A1 | 8/2004 | Blischak | |
| 2005/0003211 A1 | 1/2005 | Harada | |

FOREIGN PATENT DOCUMENTS

WO          WO 8603978  A  *  7/1986

* cited by examiner

FLUID FLOW CONTROL SYSTEM HAVING CAPILLARY FLUID FLOW RESTRICTOR

BACKGROUND OF THE INVENTION

The invention generally relates to systems and methods for controlling the infusion of medical fluids and, more particularly, to a fluid flow restrictor placed in an infusion line to achieve a more uniform rate of flow through that line while reducing the possibility of contaminants being conducted.

Infusion of fluids is one of the most widespread procedures in medicine. Infusion systems deliver liquid therapeutic substances (e.g. drugs in solution, saline, nutrients) to patients typically through veins and arteries, but also into interstitial spaces as well. Every infusion is driven by some source of pressure. Two common sources of fluid pressure for causing the infusion of medical fluids into a patient are gravity and positive pressure infusion pumps. The medical fluids are typically delivered through sterile, single-use, disposable fluid administration sets that comprise tubing and a cannula or catheter and perhaps an administration port or ports along the tubing for the infusion of additional medical fluids.

Infusion systems operating by gravity typically use a container of the medical infusion fluid suspended above the patient. In gravity infusion the pressure for infusing the medical fluid is produced by the very weight of the medical fluid itself. In practice, this is effected by suspending the container higher than the patient. Then the pressure of the fluid produced by gravity is high enough to overcome the counter pressure of the patient's circulatory system and thus allows for infusion of the medical fluid into the patient. In such a system, the magnitude of the pressure depends on the height of the container. However, as the fluid level in the container decreases, the pressure decreases and the rate of flow decreases. A varying rate of flow is undesirable for some medications as it has been found that a uniform flow rate of medical fluid has a more predictable treatment effect on the patient.

Furthermore, the requirement that the container of medical fluid must be suspended above the patient in a gravity system has made such systems impractical for use with ambulatory patients. Many surgical procedures today may be completed on an "out patient" basis. In many cases, the surgical procedure can be completed in less than a few hours and the patient may leave the health care facility in an "ambulatory" state. Yet the infusion of medical fluid after completion of the procedure is necessary for the patient's well being. The same is true for patients who have been released after extended stays at health care facilities. The continued infusion of medical fluids may be necessary for them. Whether that medical fluid is pain medication, nerve block (anesthetic), chemotherapy, or other, the continued infusion of that fluid into the patient may be necessary.

Because of this more and more common situation of an ambulatory patient with a continuing need for infusion, ambulatory infusion pumps have been developed. Such pumps can be carried by the patient at a position lower than the patient's heart, such as on the patient's belt because they use a positive pressure source. The pressure source of these pumps is strong enough to force the infusion fluid into the patient regardless of the location of the pump in relation to the patient's heart. However, such ambulatory infusion pumps must be relatively inexpensive since they are personal in nature and it is desirable that they be disposable by the patients after the treatment has been completed. Because of this need to create a lower cost and disposable ambulatory pump, many do not produce flow rates that have the desired level of uniformity.

In most cases, the mechanism used to apply pressure to the medical fluid to achieve infusion is not linear across its entire range of operation. In many cases, the amount of pressure exerted on the medical fluid when the pump is full differs from the amount of pressure when the pump is almost empty. Without further intervention, the flow rate will be correspondingly variable and non-uniform. Thus some manufacturers include fluid flow restrictors in the fluid line leading to the patient. Such flow restrictors "restrict" the flow rate of medical fluid to the patient to a level that will achieve the desired therapeutic effect. Cost considerations require that such flow restrictors be produced at low cost, yet be as accurate as possible.

To achieve the advantages of a portable ambulatory pump, several types of mechanisms have been suggested. Because of the needs to control cost and limit complexity, and to function for an ambulatory patent, a mechanical power source has proven to be more desirable.

Of the numerous mechanical structures that have been used as a pumping chamber in portable infusion pumps, one structure is of particular interest. This structure comprises an elastomeric membrane that is stretched beyond its at-rest configuration by the loading of medical fluid into it. The membrane's tendency to return to the contracted configuration provides the necessary mechanical power to move fluid through a tube to a patient. As the membrane tends to return to its at-rest configuration, the medical fluid within it is expelled out of the membrane, through the administration set, and into the patient. An elastomeric pumping mechanism has several features which make it attractive for such an application. Firstly, an elastomeric structure is relatively inexpensive to manufacture. Secondly, it has an operational simplicity that enhances its appeal for use in devices which are to be operated by lay persons.

However, an elastomeric membrane does not address the problem encountered at the end of a pumping cycle that is caused by the inability of an elastomeric membrane to maintain a constant pressure within the fluid chamber as the membrane approaches its unstretched state. With some, the membrane snaps back to its at-rest configuration as it nears that state. This results in a period of non-uniformity in the flow rate. As is well known, constant pressure within the pumping chamber during a pumping operation from beginning to end is very much desired to obtain a uniform dispensing rate.

One portable pump that takes these features into account is the ReadyMED pump made and distributed by the ALARIS Products division of Cardinal Health, San Diego, Calif. It includes a housing that stretches an elastomeric membrane into its region of nonlinear elasticity. To do this, the housing is formed with a surface that has a predetermined contour that is circumscribed by a periphery. The elastomeric membrane is then attached to this periphery to position the membrane over and across the contoured surface of the housing. This stretches the membrane into its region of nonlinear elasticity, and creates a fluid chamber between the surface of the housing and the elastomeric membrane. When the fluid chamber is filled with medical fluid, the stretched membrane generates a substantially uniform pressure on the fluid within the chamber for a uniform discharge of the fluid from the chamber.

There are several types of flow restrictors available. One example is a tube clamp that may be set by the nurse to pinch the infusion tubing partially closed to achieve a desired flow rate. Although these are simple devices and relatively inexpensive, most tubing will react to the continued application of pressure from a pinch clamp and the flow rate will vary. A more precise means of restricting the flow is desired.

Another device used as a flow restrictor is a capillary tube. With the principal flow restrictor comprising a capillary element, the extent to which the restrictor limits the fluid flow rate is determined by the length and cross-sectional area of the capillary element itself. These dimensions are selected based on the input pressure from the pressure source to deliver the liquid medicament at a predetermined flow rate. If the capillary element is to be maintained within the housing, it becomes difficult to substantially lengthen the capillary element without requiring a re-design of the housing. To avoid such a re-design, the internal diameter of the capillary element may be varied; however, with the small internal diameters utilized in the flow restrictor, such as a capillary of about 0.041 mm (0.0016 inch) in diameter, it becomes difficult to consistently manufacture capillary elements having the required precise internal diameter. It should be noted that variances in diameter can average out over the length of the capillary element but as noted above, the length of the element is limited when it is disposed within the housing, thereby limiting the extent to which the effect of variances along the length of the capillary element can be minimized.

Flow rates such as about 48 milliliters ("ml") in twenty-four hours or even slower flow rates are desirable in certain circumstances. As an example only, it is sometimes desirable to deliver 36 ml, 48 ml, or 60 ml of a medical liquid in three, four, or five days.

A further limitation with present infusion capillary tube systems is that because of the diameter involved, capillary tube fluid flow restrictors can become easily clogged. If an infusion line becomes clogged, fluid flow will slow or stop. Such a stoppage in treatment is undesirable for a patient who may depend on the medication for pain relief or for other reasons.

Currently, some pumps having elastomeric drive devices use glass capillary tubes with a very small inside diameter and a macroscopic outside diameter. This type of tube has several drawbacks associated with its use. It is difficult to obtain an adequate seal with the outside diameter of the glass because of the smooth nature of glass. Due to the cleaving operation by which the glass is cut, the outside edges of the outside diameter are sharp and can create particulate matter that may enter the fluid flow stream. This particulate can occlude the inside of the capillary, especially when the glass capillary is inserted into a fitting or a flexible sleeve. This problem has been resolved in the past by roughing or flame polishing the edges of the glass but which could again result in particulate that can occlude the capillary or which can create additional labor steps. Finally, since the cut edge of the glass capillary and the exit hole are on the same plane, these restrictors are also more likely to become clogged by particulate which comes to rest on this cut edge in close proximity to the exit hole. Thus, it is advantageous to have a fluid flow restrictor that is capable of reducing the flow rate while being less prone to clogging.

Hence those skilled in the art have recognized a need for a fluid flow restrictor that is less prone to clogging. Yet a further identified need is for a flow restrictor that can be manufactured more cost effectively and can use interchangeable parts with restrictors of differing sizes. The invention fulfills these needs and others.

SUMMARY OF THE INVENTION

In accordance with aspects of the invention, there is provided a fluid flow restrictor having a capillary tube to restrict the flow to a desired rate. In accordance with some aspects of the invention, a chamber is provided that separates contaminants from the flow of medical fluid from a reservoir before they reach the capillary tube.

In one aspect, there is provided a fluid flow restrictor for regulating the flow rate of fluid through a fluid supply tube. The supply tube comprises a distal end and an internal fluid passageway with a supply tube inner cross-section, the restrictor comprising a chamber having a distal end and a proximal end, the proximal end of which is in fluid communication with the distal end of the supply tube wherein fluid from the supply tube flows into the chamber through the proximal end of the chamber. The chamber may be configured with an inner chamber cross-section that is same or larger than the supply tube inner cross-section, and a capillary tube having a capillary tube inner cross-section that is smaller than the supply tube inner cross-section and smaller than the chamber inner cross-section. The capillary tube is preferably configured with a proximal end extending into the chamber at a desired length from the distal end of the chamber, wherein the length and the capillary tube inner cross-section are selected to result in a desired flow rate. The relative smallness of the inner cross-section of the capillary tube as compared to the inner cross-sections of the chamber and the supply tube results in filtering of contaminants into the chamber. In addition, the chamber volume resulting from the selected length of the chamber and the selected chamber inner cross-section slows the instantaneous velocity of the fluid from the supply tube so that contaminants will fall out of solution of the fluid and into the chamber.

In other more detailed aspects, the flow capillary tube is surrounded by a sleeve over less than the entire length of the capillary tube, wherein the sleeve mounts the tube such that the proximal end of the tube projects into the chamber. The fluid flow restrictor further comprises a housing surrounding the sleeve and interconnecting with the distal end of the fluid supply tube forming the chamber between the distal end of the fluid supply tube and the sleeve wherein all flow through the chamber must proceed through the capillary tube.

In additional more detailed aspects, the restrictor tube has a distal end that is in fluid communication with a distal segment of tube that conducts fluid flowing through the restrictor tube to a downstream location at the flow rate controlled by the capillary tube. The capillary tube is surrounded by a sleeve over less than the entire length of the capillary tube, wherein the sleeve mounts the capillary tube such that the proximal end of the capillary tube projects into the chamber. The sleeve may include a radially-outwardly extending mounting flange. The restrictor tube further comprises a first housing surrounding the sleeve and interconnecting with the distal end of the fluid supply tube forming the chamber between the distal end of the fluid supply tube and the sleeve, a second housing surrounding the sleeve and interconnecting with a downstream segment of the fluid supply tube into which the capillary tube feeds fluid. The first and second housings are mounted over the sleeve and may be configured to abut each other or the optional mounting flange.

In other aspects in accordance with the invention, there is provided an infusion system comprising a pump, a supply tube segment in fluid communication with the pump to conduct fluid from the pump, the supply tube segment having a distal end and a supply tube inner diameter, and a capillary flow restrictor in fluid communication with the distal end of the supply tube segment for receiving fluid from the pump and controlling the flow rate of that fluid, the capillary flow restrictor comprising a housing connected with the supply tube segment for receiving fluid from the pump, the housing having a proximal end, a sleeve disposed within the housing and having a proximal end, the sleeve disposed so that the proximal end of the sleeve is displaced from the proximal end of the housing, thereby forming a chamber having an inner chamber cross-section. The capillary flow restrictor further comprises a capillary tube mounted partially within the sleeve, the capillary tube having an inner cross-section smaller than the chamber inner cross-section and having a length, the capillary tube inner cross-section and length selected to provide a desired flow rate through the capillary tube, the capillary tube having a proximal segment extending outwardly from the sleeve and projecting into the chamber, the inner cross-section of the chamber selected to be larger than or equal to the inner cross-section of the fluid supply tube so that the chamber volume resulting from the selected length of the chamber and the selected chamber inner cross-section slows the instantaneous velocity of the fluid received from the supply tube so that contaminants will fall out of solution of the fluid and into the chamber, whereby such separated contaminants will not be conducted by the capillary tube.

Other detailed aspects include the flow restrictor comprises a capillary tube surrounded by a sleeve over less than the entire length of the capillary tube, wherein the sleeve mounts the capillary tube such that the proximal end of the capillary tube projects into the chamber, the sleeve having a radially-outwardly extending mounting flange, a first housing surrounding the sleeve and interconnecting with the distal end of the fluid supply tube forming the chamber between the distal end of the fluid supply tube and the sleeve wherein all flow through the chamber must proceed through the restrictor tube, a second housing surrounding the sleeve and interconnecting with a downstream segment of the fluid supply tube into which the capillary tube feeds fluid, and the first and second housings mounted over the sleeve and abutting the mounting flange.

Other detailed aspects include the flow restrictor having the capillary tube molded into a solid member over less than the entire length of the capillary tube, wherein the solid member mounts the capillary tube such that the proximal end of the capillary tube projects into the chamber. The flow restrictor further comprises a first housing surrounding a portion of the solid member and interconnecting with the distal end of the fluid supply tube forming the chamber between the distal end of the fluid supply tube and the solid member; a second housing surrounding the solid member and interconnecting with a downstream segment of the fluid supply tube into which the capillary tube feeds fluid. the first and second housings mounted over the solid member and abutting each other.

In accordance with method aspects of the invention, there is provided a method for restricting the flow of medicament through a fluid supply tube comprising pumping medicament into the fluid supply tube at a first instantaneous velocity, slowing the velocity of medicament through the fluid supply tube at a point downstream to a second instantaneous velocity that is less than the first such that contaminants in the medicament fall out of solution and are separated from the liquid of the medicament, and conducting the liquid of the medicament from the point where the contaminants are separated preventing the contaminants from further downstream flow.

These and other aspects, features, and advantages of the present invention will become apparent from the following detailed description of the preferred embodiments which, taken in conjunction with the accompanying drawings, illustrate by way of example the principles of the invention.

DETAILED DESCRIPTION OF THE INVENTION

Figure 1:
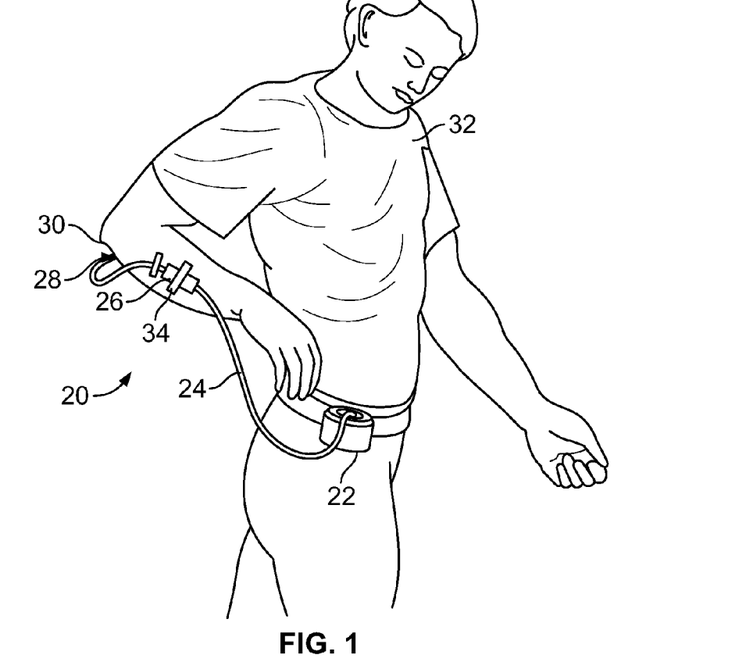
FIG. 1 is a view of a patient using an ambulatory pump mounted to his belt, the pump having a fluid administration set connected to it to conduct the medicament in the pump to the patient's elbow, the administration set including a fluid supply tube segment, a flow restrictor, an output tube segment, and a sharp cannula.
Figure 2:
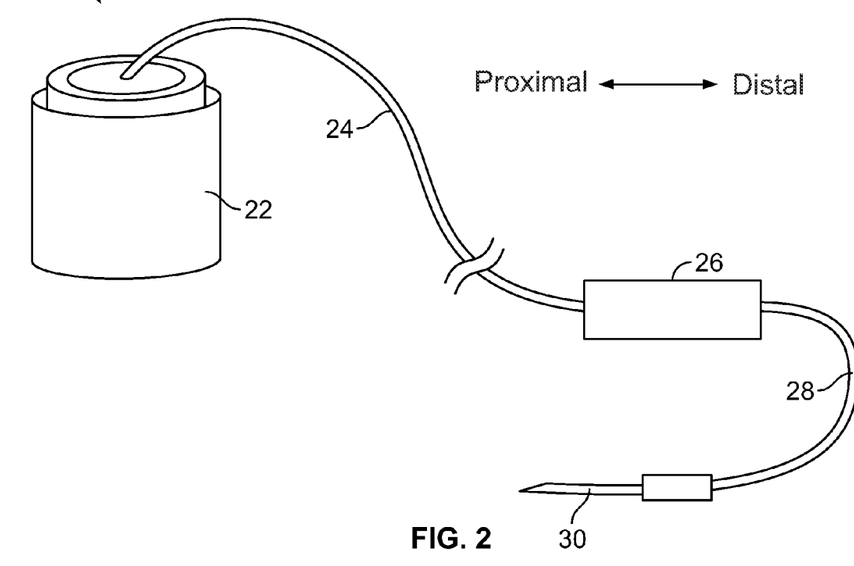
FIG. 2 is a view of the ambulatory pump system shown in FIG. 1 in which the pump is driven with an elastomeric membrane, conduits, a fluid flow restrictor, and a sharp cannula for delivering the medical fluid supplied by the pump to the patient.

Referring now to the drawings in more detail in which like reference numerals refer to like or corresponding devices among the views, there is shown in FIGS. 1 and 2 a view of an embodiment of an infusion system 20 having a pump 22, a medicament supply tube segment or pump-side tube segment 24 from the pump, a fluid flow rate restrictor 26, a patient delivery tube segment or patient-side tube segment 28, and a sharp cannula 30 for inserting into the patient to perform the infusion. In FIG. 1, it will be noted that the restrictor has been affixed to the patient 32 with tape 34 to stabilize the position of the cannula and control the temperature of fluid entering the restrictor assembly. This approach is meant to provide a broad illustration only and not meant to be restrictive of the use of the invention. Other techniques well known to those skilled in the art for mounting pumps to or with a patient, puncturing the patient, and stabilizing a tube, restrictor, or other devices may be employed as needed. Additionally, the size of the restrictor 26 has been exaggerated in this case for clarity of illustration.

The fluid infusion system 20 can be used for a wide variety of therapies such as pain, spasticity, cancer, and other medical conditions. The fluid infusion system 20 operates to infuse a therapeutic substance at a pre-determined rate into the patient 32. The therapeutic substance is a product or substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances are substances intended to have a therapeutic effect yet are not easily classified such as saline solution, fluoroscopy agents, and the like.

Figure 3:
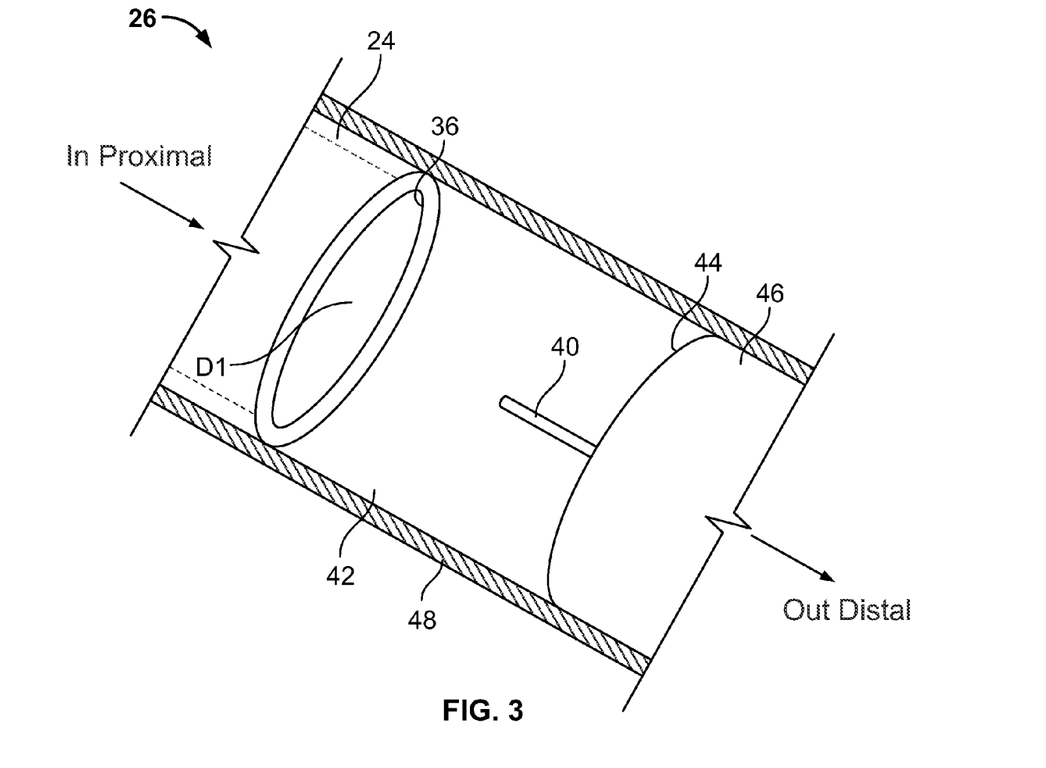
FIG. 3 is a partial cross-sectional view of a fluid flow restrictor shown in accordance with aspects of the invention showing a capillary tube projecting into a fluid contaminants separation chamber.

Referring now to FIG. 3, an embodiment of a fluid flow rate restrictor 26 in accordance with aspects of the invention is provided. The pump-side tube segment 24 is shown facing a capillary tube 40 that forms a part of the restrictor 26. The pump-side tube segment includes a lumen opening 36 having a certain size (i.e. dimension) D1. Fluid from the pump 22 will be received from the lumen opening of the pump-side tube segment 24 into a chamber 42. The chamber is formed by the pump-side tube segment 24 at the proximal end, and the distal end of the chamber is formed by the proximal end 44 of a sleeve 46 that surrounds and mounts the capillary tube 40. The outer wall of the chamber is provided by a housing 48 that tightly fits over the fluid supply tube segment 24 and the sleeve 46 of capillary tube 40 in a fluid-tight fashion. As will be described in more detail below, the chamber has a volume selected to cause medicament entering the chamber 42 from the pump through the pump-side tube segment 24 to decrease in instantaneous velocity to a level where contaminants in the medicament fall out of the solution of the medicament thereby separating from the medicament. Those contaminants may then fall to the wall 48 provided by the housing. Because the capillary tube projects into the chamber by a certain distance and is not flush with the proximal end 44 of the sleeve 46, it is much less likely that those separated contaminants will find their way into the capillary tube opening. In this way, the chamber performs a filtering function. In addition, the capillary tube may be eccentrically or oddly shaped to further precipitate filtering of contaminants.

Figure 4:
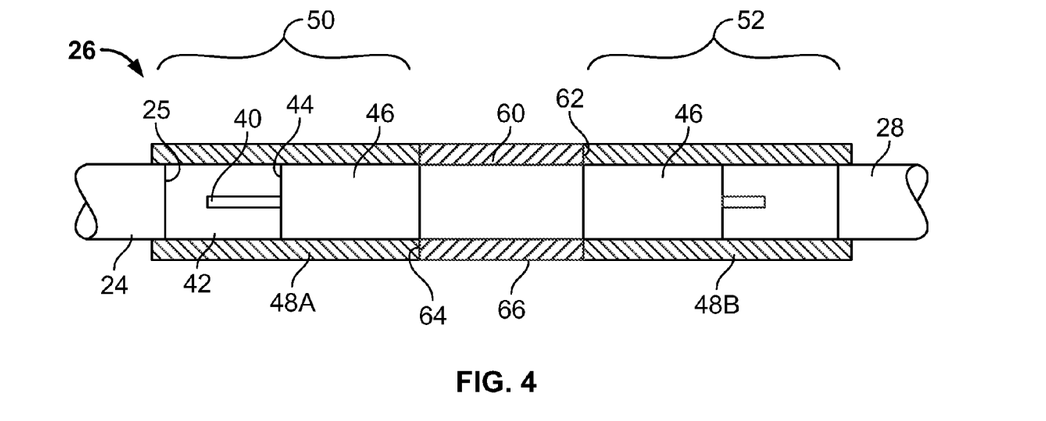
FIG. 4 is a partial cross-sectional side view of the fluid flow restrictor of FIG. 3 showing the mounting configuration for the capillary tube and over-bonded sleeve.

Turning now to FIG. 4, a partial cross-sectional side view of the restrictor of FIG. 3 is shown. The fluid supply tube segment 24 has a distal end 25 that forms a part of the chamber 42. As can perhaps more clearly be seen in FIG. 4, the contaminant-separating chamber 42 is formed by that distal end 25 of the fluid supply tube segment, the proximal end 44 of the capillary tube mounting sleeve 46, and the housing 48A. As illustrated, capillary tube 40 is preferably projected into the chamber to further aid filtering of contaminants. Also illustrated in FIG. 4, the patient-side tube 28 is connected to the restrictor 26 by the housing 48B. The housing consists of two parts, section 48A on the proximal end 50 of the restrictor, and section 48B on the distal end 52.

The sleeve 46 around the capillary tube 40 may be formed of polyvinylchloride (PVC). The capillary tube 40 is slid into the sleeve and located as desired. Adhesive may be applied at one end of the sleeve at the capillary and will wick into the interface of the sleeve and capillary tube to permanently attach the sleeve to the capillary tube. In a preferred embodiment the capillary tube 40 is disposed within the sleeve 46 by adhesive bonding for example at its proximal end. Rigidity of the sleeve will protect the capillary tube from breakage due to extreme inadvertent bending.

As illustrated in FIG. 4, an optional mounting flange 60 may be mounted on the sleeve 46. The mounting flange may be centered on the sleeve and may also be formed of PVC. In one embodiment, the mounting flange is a shorter sleeve (e.g. 60) slid over the first sleeve (e.g. 46) and held in position by adhesive or other means. The mounting flange provides distal 62 and proximal 64 abutment surfaces for the housing 48B, 48A to facilitate manufacture and assembly of the restrictor 26.

In one or more configurations (not shown), mounting flange 60 may be omitted. In such configurations, housing sections 48A and 48B may be configured such that the distal end of housing section 48A and the proximal end of housing section 48B are approximately abutting.

In a further embodiment, the sleeve 46 comprises a hard-plastic housing that is formed by being over-molded around the capillary tube 40. The amount of overlap of the housing over the pump-side tube segment 24 and the patient-side tube segment 28 is not to scale in FIG. 4 and may actually be more than shown. Although not shown, the housing may have stop shoulders located internally to receive the pump-side tube segment and patient-side tube segment and limit their length of insertion into the housing.

Figure 5:
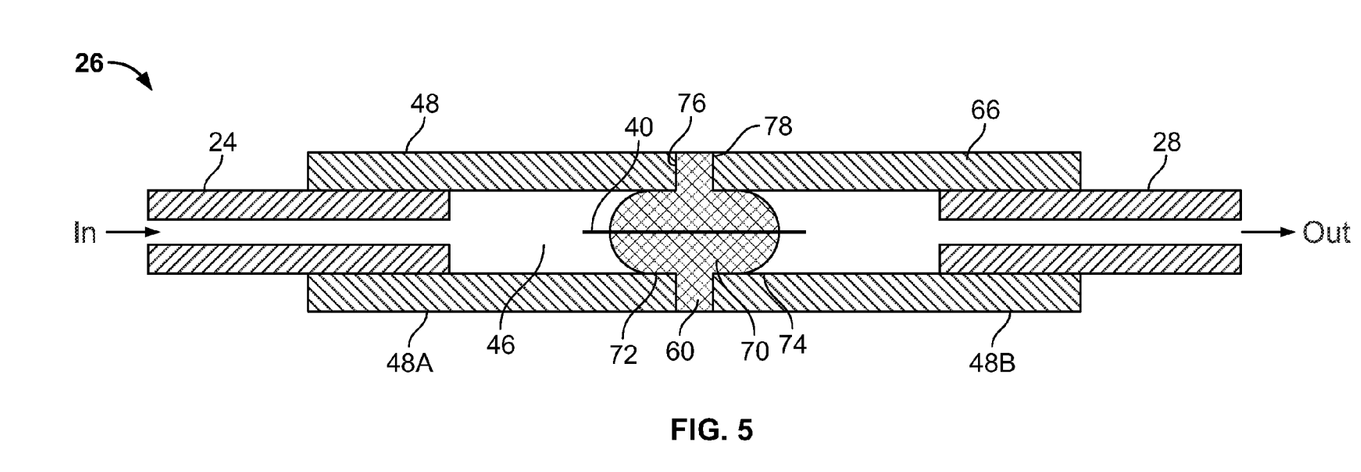
FIG. 5 is a partial cross-sectional side view of another embodiment of the flow restrictor of the present invention showing the capillary tube, mounting sleeve, and housing coupled to fluid conduits or tubes in which the capillary tube extends beyond the mounting sleeve, for conducting medicament to the patient.

Referring now to FIG. 5, an alternate embodiment is shown in which the sleeve 70 of the capillary tube 40 differs from the embodiment of FIG. 4. In this case, the sleeve may be formed by overmolding of PVC of another plastic material on the capillary tube and is configured to provide not only protection for the capillary tube and to provide proximal 72 and distal 74 mounting surfaces for the housing 48, but also proximal 76 and distal 78 abutment surfaces for the housing. As in all the other configurations, the capillary tube may be configured to project out of the sleeve in both the proximal and distal directions. Also, flange 60 may be configured to extend outward to the distance similar to that of the housing outer surface to form a relatively smooth outer surface 66. The patient will feel less discomfort with a smooth outer surface design than with other designs having an uneven outer surface.

Figure 6:
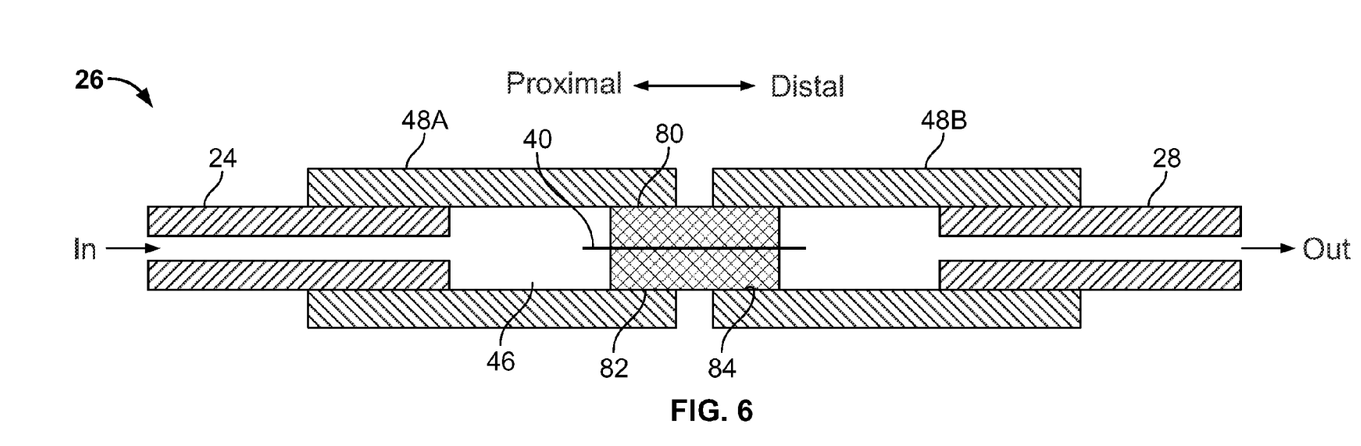
FIG. 6 is a partial cross-sectional side view of yet another embodiment of the flow restrictor of the present invention showing the capillary tube, mounting sleeve, and housing coupled to fluid conduits or tubes in which the capillary tube extends beyond the mounting sleeve, for conducting medicament to the patient.

Referring now to FIG. 6, another alternate embodiment is shown in which the sleeve 80 of the capillary tube 40 differs from the previous embodiments. In this embodiment, the sleeve 80 may also be formed by overmolding of PVC or another plastic material on the capillary tube. The sleeve is configured to provide protection for the capillary tube and to provide proximal 82 and distal 84 mounting surfaces for the housing (48A, 48B). No abutment surfaces for the housing are provided and a gap may exist between the two housing components 48A and 48B. It should also be noted that this embodiment is configured such that the sleeve 80 has a length and location in relation to the capillary tube 40 so that both ends of the capillary tube project beyond the ends of the sleeve. This eliminates the possibility that the capillary tube could be improperly oriented when installed in the restrictor 26. This will also reduce cost in the manufacturing process thus making it widely available to all patients with differing access to health care.

Figure 7:
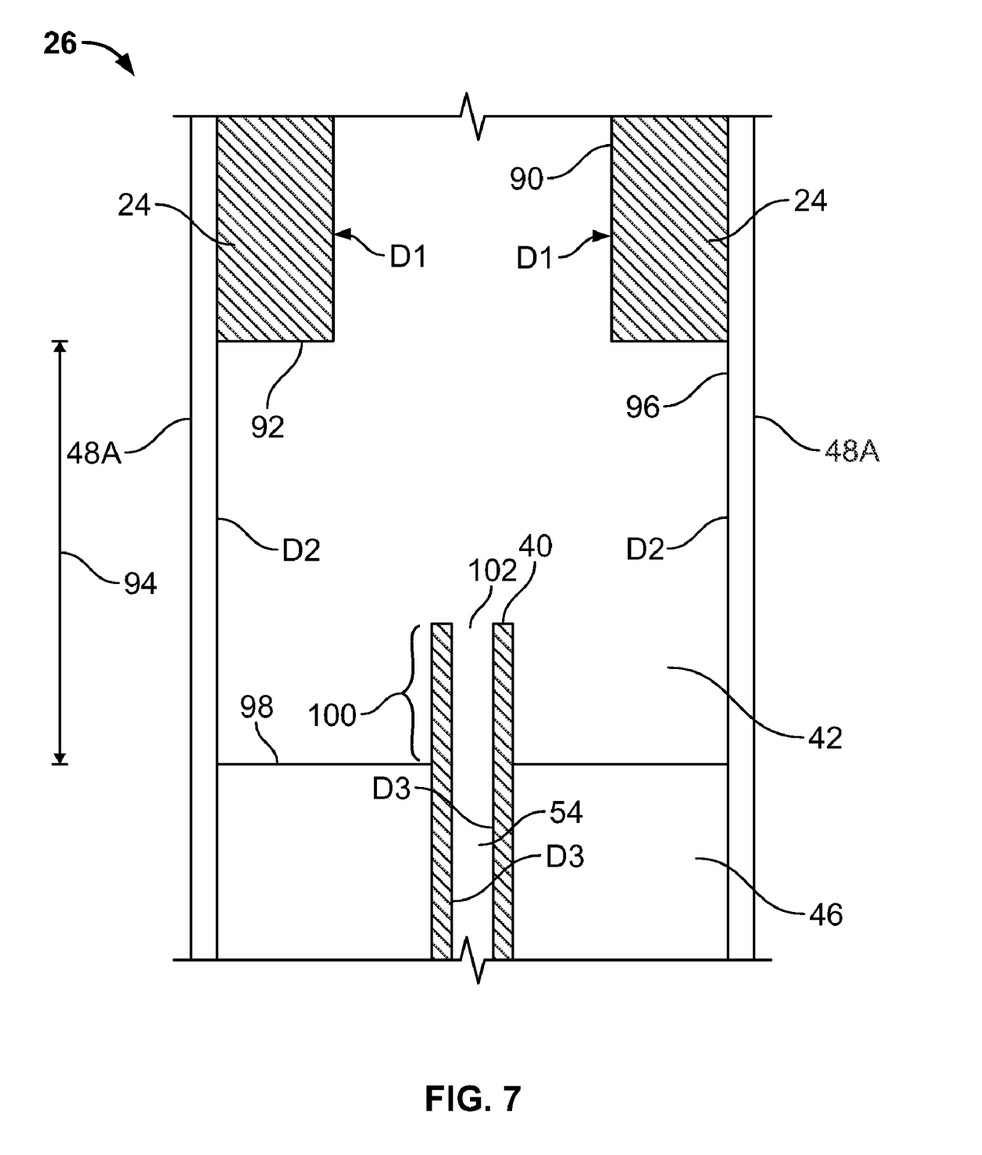
FIG. 7 provides a cross-sectional view of part of the diagram of FIG. 6 showing the capillary tube, contaminant separation chamber, and conduit walls.

Turning now to FIG. 7, further information on the relative sizes of the components of the chamber 42 is provided. Dimension D1 is the inner surface dimension of the pump-side tube segment 24. Dimension D2 is the inner surface dimension of the housing which surrounds both the pump-side tube segment and the sleeve 46 that in turn surrounds the capillary tube 40. Dimension D3 is the inner surface dimension of the lumen 54 of the capillary tube 40. D2 is larger than D1 which is larger than D3. The internal fluid passageway 90 of the pump-side tube segment with a first inner dimension D1 is in fluid communication with a proximal end 92 of a chamber 42. The chamber 42 has a length 94 and a chamber wall 96. The chamber has a second inner dimension D2 that is larger than the first inner dimension D1. A capillary tube 40 having a third inner dimension D3 is provided. The capillary tube 40 is located at a distal end 98 of the chamber and has a length 100 projecting into the chamber. The third inner dimension D3 is smaller than the first D1 and the second D2 inner dimensions. The inner dimensions D1, D2, D3 along with the lengths 94 and 100 are selected to result in optimal filtering properties with minimal opportunity of damage to the capillary tube during manufacture or use.

As used herein, 1 "mil inch" shall be equal to $1/1000$ of an inch and "mil-inches" shall indicate more than one mil-inch. Also, note that the flow restrictor, sleeve, and capillary may have circular cross-sectional areas thus, although their inner surface dimensions may be referred in terms of diameters, reference to diameters are not intended to limit the invention to circular/cylindrical objects.

Referring to the embodiments in FIGS. 4 through 7, the sleeve (i.e. 46, 70, 80) can be injection molded around the capillary tube 40. Alternatively, the sleeve (i.e. 46, 70, 80) can be co-extruded around the capillary tube during its manufacturing process.

Previous flow restrictors had the end of the capillary tube 40 flush with the end of the sleeve. In accordance with an aspect of the present invention, the capillary tube 40 projects outward from the sleeve and into the chamber 42. In operation, fluid flows from the pump-side tube 24 at relatively high velocity and into the chamber 42 having a much larger volume. Once it reaches the chamber, the fluid velocity slows. Any contaminants being carried in the fluid will leave solution and settle to the bottom of the chamber 42, away from the opening 102 to the capillary tube 40.

The above-mentioned components of the restrictor 26 may be color coded to indicate the intended fluid flow rate of the restrictor. Such color coding provides a visual indication that the correct restrictor is assembled in the correct model.

The capillary tube 40 places a maximum limit on the flow rate of fluid out of the restrictor 26. The capillary tube may be non-adjustable and thus pre-selected during manufacture to provide a given maximum fluid flow rate for fluid flowing out of the restrictor. In a preferred embodiment the capillary tube 40 is made of glass and defines a very small bore 102 in fluid communication with the chamber 42.

With the flow regulator near the connecting means, the restrictor 26 can be placed on the patient's skin. The patient's body heat maintains the liquid passing through the capillary lumen 54 at a relatively constant temperature, regardless of changes in the ambient air temperature. When the infusion site is near the subclavian vein for example, the temperature is about 92 degrees F. (33.3 degrees C.). This relatively constant temperature provides a relatively constant liquid viscosity in the restrictor 26 and thus a more constant fluid flow rate through the bore 54.

While several forms of the invention have been illustrated and described, it will also be apparent that various modifications can be made without departing from the spirit and scope of the invention. Accordingly, it is not intended that the invention be limited except by the appended claims.

What is claimed is:

1. A fluid flow restrictor for regulating the flow rate of fluid through a fluid supply tube, the supply tube having a distal end and having an internal fluid passageway with a supply tube inner cross-sectional area, the restrictor comprising:
    a chamber having a distal end and a proximal end, the proximal end of which is in fluid communication with the distal end of the supply tube wherein fluid from the supply tube flows into the chamber through the proximal end of the chamber, the chamber having a chamber length and a chamber inner cross-sectional area that is larger than the supply tube inner cross-sectional area;
    a restrictor tube having an inner cross-sectional area that is smaller than the supply tube inner cross-sectional area and smaller than the chamber inner cross-sectional area, said restrictor tube having a length, wherein the restrictor tube length and the restrictor tube inner cross-sectional area are configured to result in a desired flow rate, the restrictor tube having a proximal end extending into the chamber from the distal end of the chamber; and
    a sleeve surrounding the restrictor over less than the entire length of the restrictor tube, wherein the sleeve mounts the restrictor tube such that the proximal end of the restrictor tube projects into the chamber.

2. The fluid flow restrictor of claim 1, further comprising a housing surrounding the sleeve and coupled with the distal end of the fluid supply tube forming the chamber between the distal end of the fluid supply tube and the sleeve.

3. The fluid flow restrictor of claim 1 wherein the supply tube has the same cross-sectional area as the chamber.

4. The fluid flow restrictor of claim 1 wherein the inner cross-sectional area of the restrictor tube is much less than the inner cross-sectional area of the chamber.

5. The fluid flow restrictor of claim 1 wherein the restrictor tube has a distal end that is in fluid communication with a distal segment of a tube that conducts fluid flowing through the restrictor tube to a downstream location at the flow rate controlled by the restrictor tube.

6. The fluid flow restrictor of claim 1 wherein the sleeve comprises a radially-outwardly extending mounting flange, the fluid flow restrictor further comprising:
    a first housing surrounding the sleeve and interconnecting with the distal end of the fluid supply tube forming the chamber between the distal end of the fluid supply tube and the sleeve wherein all flow through the chamber proceeds through the restrictor tube;
    a second housing surrounding the sleeve and interconnecting with a downstream segment of fluid tube into which the restrictor tube feeds fluid; and
    the first and second housings mounted over the sleeve and abutting the mounting flange.

* * * * *